United States Patent [19]

Härle

[11] Patent Number: 5,653,710
[45] Date of Patent: Aug. 5, 1997

[54] OSTEOSYNTHETIC FORCE TRANSMITTING MEMBER

[76] Inventor: Anton Härle, Drechslerweg 40, Münster, Germany, D-48161

[21] Appl. No.: 342,499

[22] Filed: Nov. 21, 1994

[30] Foreign Application Priority Data

Nov. 23, 1993 [DE] Germany .................. 43 39 804.9

[51] Int. Cl.⁶ .................................................. A61B 17/68
[52] U.S. Cl. ................................................ 606/73; 606/61
[58] Field of Search .......................... 606/73, 72, 69, 606/70, 71, 61, 60, 65, 66, 104

[56] References Cited

U.S. PATENT DOCUMENTS

| | | | |
|---|---|---|---|
| 5,019,078 | 5/1991 | Perren et al. ....................... | 606/61 |
| 5,129,900 | 7/1992 | Asher et al. ....................... | 606/61 |
| 5,269,784 | 12/1993 | Mast .................................. | 606/69 |

FOREIGN PATENT DOCUMENTS

| | | |
|---|---|---|
| 3630863 | 3/1988 | Germany . |
| 3800052 | 7/1989 | Germany . |

*Primary Examiner*—Guy V. Tucker

[57] ABSTRACT

An osteosynthetic member, such as a bone screw, is provided with a weakened zone which breaks in response to the application of excessive bending, shearing and/or other stresses. The location of the weakened zone is selected in such a way that it is spaced apart from a bone into which an externally threaded section of the member extends. This ensures that the protruding part of the externally threaded section can be engaged by pliers, by a screwdriver or another suitable tool to withdraw the externally threaded section from the bone.

25 Claims, 2 Drawing Sheets

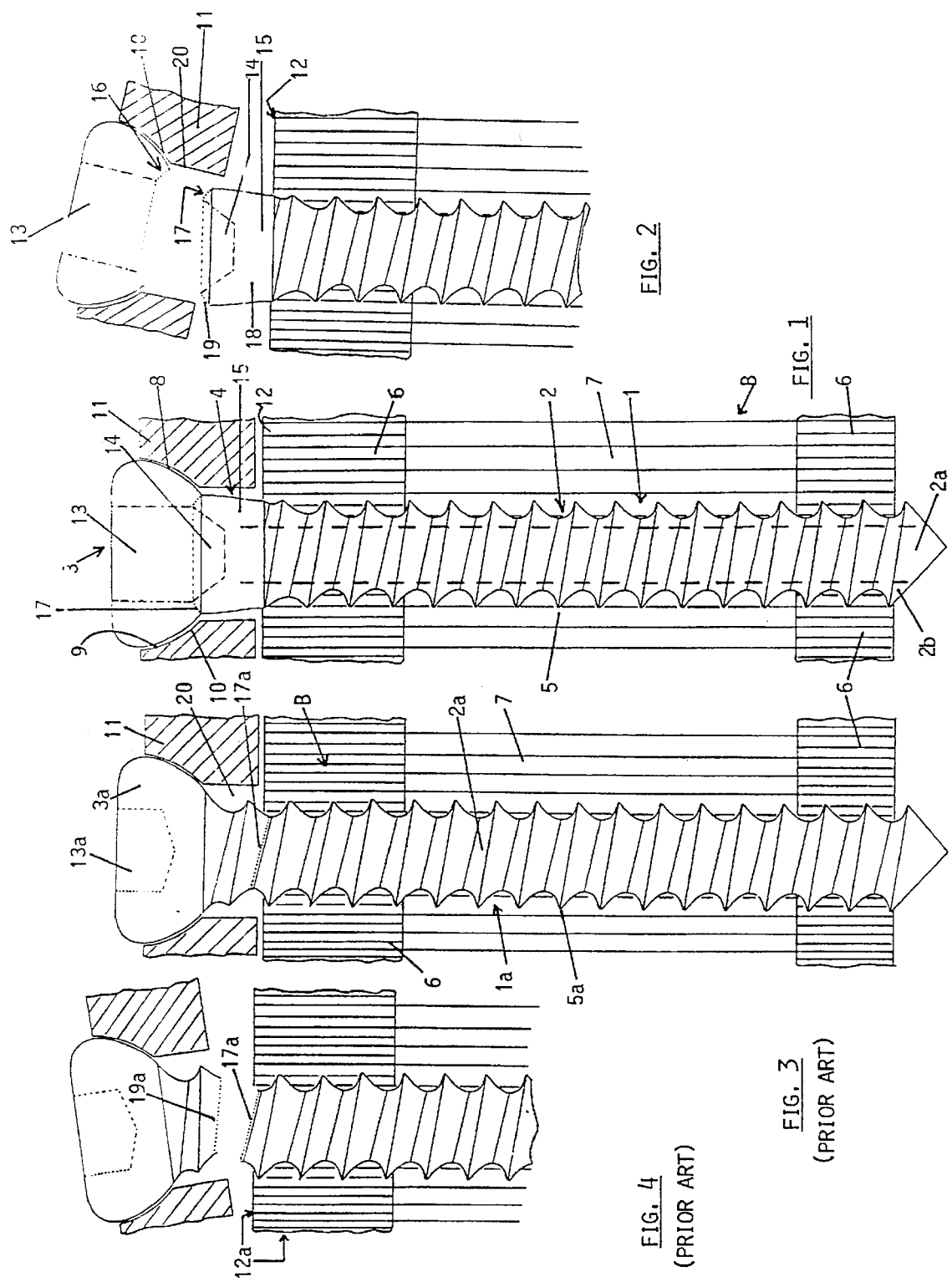

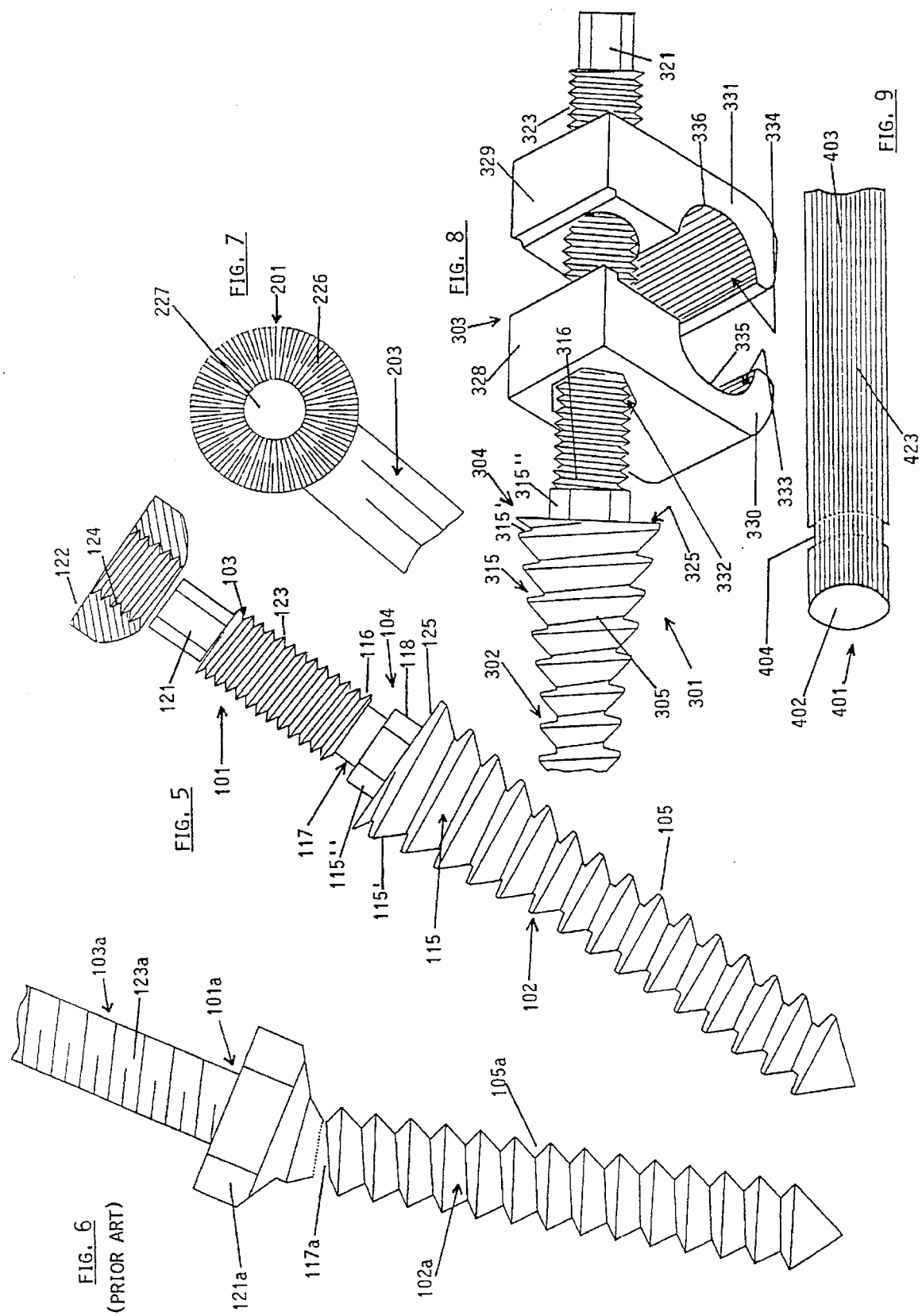

OSTEOSYNTHETIC FORCE TRANSMITTING MEMBER

BACKGROUND OF THE INVENTION

The invention relates to the art of uniting parts of fractured bones by mechanical means, such as by plates or the like. More particularly, the invention relates to improvements in osteosynthetic force transmitting members or connectors which can be used, for example, to affix parts of broken bones to plates or other types of positioning means.

Osteosynthetic force transmitting members of the present invention can constitute screws, threaded inserts, pins, plates, rod-shaped load carriers, component parts of prostheses and/or surgical instruments (e.g., instrument, which can be used to drill holes or bores in selected portions of bones).

Osteosynthetic force transmitting members which can be constructed, assembled and used in accordance with the invention can be classified into several groups. A first group includes or embraces those osteosynthetic force transmitting members which are designed to constitute implants, i.e., devices which are or can be anchored directly in a bone. A second group embraces those members which constitute load bearing implants; i.e., devices which do not or need not penetrate directly into a bone. A third group embraces force transmitting members which are utilized by surgeons only in the course of an operation, e.g., to mechanically unite parts of fractured bones, and can constitute drills for making tapped bores or holes in fragments or selected portions of bones, flexible shafts or other instruments capable of being put to use preparatory to or in the course of a uniting operation.

A drawback of heretofore known osteosynthetic force transmitting members which belong to the aforediscussed groups, particularly but not exclusively to the first and second groups, is that their ability to transmit and/or stand forces is not sufficiently predictable. For example, problems can arise when a bone screw, a partially or fully threaded bone pin or another force transmitting member belonging to the aforementioned first group of such members is called upon to maintain plates, rods, bars and/or other osteosynthetic accessories in optimum positions for temporarily holding discrete bones or fragments of bones in a desired orientation relative to each other or to permanently affix discrete bones or fragments of bones to each other.

If the osteosynthetic treatment involves a bone having a hollow shaft which surrounds a medullary cavity for hematopoietic bone marrow, fatty tissue or a spongy part, it is often necessary to employ a substantially plate-like accessory which is provided with one or more holes for the shank or shanks of one or more bone screws which are driven into the bone. The parts of such bone assume the desired positions relative to each other when the plate-like accessory is properly held between a bone or an adjacent fragment of a bone and the head of the bone screw. As a rule, or in many instances, the head of each bone screw extends into a recess provided therefor in that side of a plate-like accessory which faces away from the bone. Each recess can be bounded by a concave (e.g., substantially hemispherical) surface complementary to the surface of that portion of a screw head which enters the recess when the fixing of the bone and the accessory relative to each other is completed.

The stability of the connection between several bones or between portions of a broken or otherwise damaged bone is ensured by causing the head of the screw to bear against a plate or another osteosynthetic accessory and by causing such accessory to bear against the adjacent bones or against the adjacent fragments of a particular bone. In many instances, that part of a properly inserted bone screw (namely a portion of the shank or stem) which has been caused to penetrate into a bone in order to maintain an accesory in requisite position is subjected (either exclusively or primarily) to longitudinal or tensional stresses. Bending stesses which develop when a bone screw is properly anchored in a bone and which would tend to bend or flex the inserted portion of the shank are taken up by the bone tissue which normally exhibits a certain amount of resiliency. However, that portion or section of the shank which extends from the bone is often subjected to highly pronounced mechanical stresses including bending or flexing and shearing stresses which can cause the screw to break in the region adjacent the head of the screw, namely between the external surface of the bone and the adjacent surface of an accessory in the form of a plate, rod, bar or the like. The provision of an external thread on the shank of a bone screw (such thread normally extends all the way from the tip of the shank to the head) also entails a weakening of the shank adjacent to the head, i.e., a weakening of that portion which is subjected to greatest bending and other stresses.

The likelihood of breakage of a bone screw adjacent the head, namely in the region closely adjacent the external surface of the bone and the confronting surface of an accessory generates numerous problems in actual use of such force transmitting members. If a break develops, it is normally very close to the exposed surface of the bone (i.e., at the location where the shank has penetrated into a bone or a bone fragment) so that it is difficult to extract the anchored portion of the shank from the bone. As a rule, such extraction must be preceded by time-consuming removal of those portions of the bone which are immediately adjacent the outermost part of the broken and concealed (embedded) portion of the shank. The removal of certain portions of the bone confining the broken off major portion of the shank of a broken screw is normally carried out by resorting to a tubular drill which must remove a relatively large amount of bone material in order to provide room for the application of tongs or another suitable tool (e.g., a cone) which is to extract the broken off portion of the shank from the bone. Such procedure results in pronounced and highly undesirable weakening of the bone because the thus weakened bone or bone fragment is likely to break at the locus of the hole or bore which confined the broken off portion of the shank. It is often necessary to transfer bone tissue from other portions of the weakened bone or from another bone in order to fill the hole or bore and/or the recesses or cavities formed by the drill and to thus increase the strength of the affected bone.

The problems which arise as a result of breakage of bone screws or analogous force transmitting members are even more acute if a force transmitting member (e.g., a pin or a screw such as a so-called pedicle screw) is used to penetrate into a vertebra forming part of the spinal column. The dimensions of a vertebra are such that it is not possible to employ more than a single pedicle screw or an analogous force transmitting member in order to establish a connection between the affected vertebra and a plate or another osteosynthetic accessory which is normally applied in order to take up forces acting in the longitudinal direction of the spinal column. Moreover, a pin or screw which is anchored in a vertebra is even more likely to break at the locus of exit from the respective vertebra because the bending or flexing stresses are increased due to the fact that a relatively long portion of the screw or pin between the vertebra and the accessory (be it a plate, a bar, a rod or the like) remains exposed, i.e., a substantial length of the force transmitting member (up to 2 cm in length) is not anchored in the vertebra and is not confined in the accessory but is exposed in a dorsal direction from the respective vertebra. This results in a long lever arm and greatly increases the likelihood of breakage of the force transmitting member between the vertebra and the accessory.

A force transmitting member which is used to affix a bone or a fragment of a bone to a plate or another accessory is likely to break on the additional ground that, at least in many instances, the area of contact between a bone or bone fragment and an accessory is very small. Therefore, only a small percentage of bending stresses acting upon the force transmitting member is converted into tensional stresses, i e., into stresses which are more likely to be withstood by the force transmitting member. All in all, breakage of a pedicle screw or another force transmitting member which is driven into a vertebra is much more likely to take place than the breakage of a bone screw or an analogous force transmitting member which is driven into a tubular bone or into a fragment of a tubular bone. It has been ascertained that approximately ten percent of force transmitting members which are driven into a vertebra are likely to break between the vertebra and the osteosynthetic accessory. Furthermore, the difficulties which develop preparatory to and during extraction of a broken portion of a force transmitting member from a vertebra are even greater than the aforediscussed problems arising in connection with the extraction of a broken portion of a bone screw from a tubular bone. It is normally necessary to remove a large portion of or even the entire root of the neural arc, i.e., of that part of a vertebra in which the shank of a pedicle screw or an analogous force transmitting member is anchored in the vertebra. This entails that it is no longer possible to reliably secure an osteosynthetic accessory to the thus damaged root. Therefore, it happens quite frequently that the surgeons decide to simply leave the broken off portions of force transmitting members in the respective vertebrae. The reason is that the removal of a broken off portion of a force transmitting member from a vertebra must be carried out with utmost care because the broken off portion of the force transmitting member is very closely adjacent to the spinal cord. As a rule, the distance of the broken off portion of a force transmitting member from the spinal cord is not more than 1–2 mm. On the other hand, a broken off force transmitting member which is left in the vertebra constitutes a potential source of problems at a later date. Therefore, it is highly desirable to remove the broken off portions of force transmitting members from the bones or bone fragments.

Conventional osteosynthetic force transmitting members and accessories are disclosed for example, in German patent application No. 36 30 863 A1 filed by Curt Kranz and published Mar. 17, 1988, and in German patent application No. 38 00 052 A1 filed by jürgen Harms et al. and published Jul. 13, 1989 (corresponding to U.S. Pat. No. 5,042,982).

OBJECTS OF THE INVENTION

An object of the invention is to provide a novel and improved osteosynthetic force transmitting member which is less likely to break at a non-accessible location than heretofore known force transmitting members.

Another object of the invention is to provide a force transmitting member which is constructed in such a way that a part of its broken off portion can be readily engaged and manipulated (e.g., withdrawn) by available tools without necessitating the removal of bone material around the embedded broken off portion.

A further object of the invention is to provide a novel and improved pin-shape, screw-shaped or otherwise configurated force transmitting member which can be utilized with available osteosynthetic accessories to ensure reliable retention of bones or portions of bones in selected positions, An additional object of the invention is to provide a novel and improved method of selecting the resistance of various portions of the above outlined osteosynthetic force transmitting member to breakage in actual use of the member.

Still another object of the invention is to provide a novel and improved combination of an osteosynthetic force transmitting member and one or more osteosynthetic accessories, A further object of the invention is to provide a novel and improved bone screw, Another object of the invention is to provide an osteosynthetic force transmitting member which can be used in conjunction with available osteosynthetic accessories, An additional object of the invention is to provide an externally threaded osteosynthetic force transmitting member wherein the presence of threads at the locus where a properly installed member extends from a bone or bone fragment does not affect the predictability of resistance which the installed member offers to shearing, bending and other stresses which tend to break the force transmitting member.

SUMMARY OF THE INVENTION

The invention is embodied in an osteosynthetic force transmitting member which comprises a first section serving to force-lockingly engage a bone, a second section which includes means for coupling the force transmitting member to an osteosynthetic accessory (e.g., to a plate or strip), and an intermediate section which is disposed between the first and second sections and constitutes a weakened part of the force transmitting member, i.e., the intermediate section is more likely to break under overload conditions than the first and/or the second section in response to the application of forces to the force transmitting member. The intermediate section includes first and second components which are of one piece with the first and second sections, respectively, and which establish between themselves a breakage zone. In accordance with a feature of the invention, the first component is accessible—upon breakage of the force transmitting member at the breakage zone—for direct engagement by a suitable displacing tool which serves to move the first section relative to the bone. In other words, it is not necessary to remove a portion of the bone adjacent the first component of the intermediate section in order to gain access to such first component subsequent to breakage of the force transmitting member at the breakage zone because the first component is accessible to the displacing tool (e.g., a wrench) at least subsequent to breakage of the intermediate section at the selected breakage zone. For example, the displacing tool can be used to terminate the force-locking connection between the bone and the first section of the force transmitting member.

The first section is preferably provided with means (such as one or more external projections in the form of ribs, threads and/or pins) for establishing a force-locking connection by anchoring the first section in the bone.

The first, second and intermediate sections of the improved force transmitting member can constitute or form part of a surgical implement, for example, an instrument which is designed to provide a selected bone with a cavity, e.g., with a tapped or untapped bore or hole. The first section of such force transmitting member or instrument is preferably designed to penetrate into a selected portion of a selected bone.

The second section of the force transmitting member can include a profiled motion transmitting part which is engageable by a tool serving to effect a movement of the first section relative to a bone in the absence of breakage of the intermediate section. The first component of the intermediate section can be provided with a surface which is configurated, dimensioned and positioned to receive and to transmit pressure to the first section, e.g., to transmit pressure in the longitudinal or axial direction of the first section, and such first component can further include a profiled motion transmitting part which is directly engageable by the displacing tool at least upon breakage of the intermediate section between the first and second components. At least one of the two profiled parts (of the second section and the intermediate section) can have a cross-sectional outline departing from a circular or truly circular outline. For example, at least one of the profiled parts can have an external and/or an internal profile which departs from a circular profile. Furthermore, at least one of the profiled parts can include a plurality of different portions which are engageable by tools serving to move the respective section relative to a bone which is form-lockingly engaged by the first section. It is possible to provide at least one of the profiled parts with a substantially conical, spherical or a part conical and part spherical surface.

At least a portion of the intermediate section can have a cross-section which is smaller than the cross-sections of neighboring portions of the first and second sections. Furthermore, at least one of the first and second sections can comprise a plurality of discrete elements.

As mentioned above, the first section of the improved force transmitting member can be provided with an external thread forming part of the means for establishing a force-locking connection between the first section and a bone. However, it is equally within the purview of the invention to provide an external thread on the intermediate and/or second section of the force transmitting member in addition to or in lieu of a thread on the first section.

The first section of the force transmitting member can include a first portion having a first cross section and a second portion having a greater second cross section and being adjacent the first component of the intermediate section. The second portion of the first section can have a substantially conical, a substantially spherical or a substantially spheroidal outline. The first section can further include a transition zone which is disposed between the first and second portions and has a smoothly curved outline. Such first section can include a thread which is shaped in such a way that its root diameter and/or its major diameter increases in a direction toward the intermediate section.

That portion of the first section which is adjacent to and of one piece with the first component of the intermediate section can have a cross section which is larger than the cross section of the first component.

The intermediate section of the improved force transmitting member can have a polygonal outline and the first section can be provided with a profiled surface which is adjacent the first component of the intermediate section.

If the second section is provided with an external thread, such thread can extend all the way from that end of the second section which is of one piece with the second component of the intermediate section to the other (e.g., free) end of the second section.

At least one section of the force transmitting member can consist of a plurality of different materials. For example, the at least one section (such as the intermediate section) can have a core consisting of a metallic material and an outer layer or shell surrounding the core and consisting of a material (e.g., a fibrous material) other than the material of the core. The second section of such force transmitting member can include an externally threaded metallic portion adjacent the intermediate section.

The improved force transmitting member can resemble or constitute an elongated screw or bolt having a head forming part of or constituting the second section and a shank including the first and intermediate sections and, if desired, a portion of the second section. That portion of the shank which constitutes the first section can be driven into a bore or hole in a bone, e.g., a hole or bore which is made by a second force transmitting member constituting the aforementioned surgical instrument.

The novel features which are considered as characteristic of the invention are set forth in particular in the appended claims. The improved osteosynthetic force transmitting member itself, however, both as to its construction and the mode of making and utilizing the same, together with additional features and advantages thereof, will be best understood upon perusal of the following detailed description of certain presently preferred specific embodiments with reference to the accompanying drawings.

BRIEF DESCRIPTION OF THE DRAWINGS

FIG. 1 is an enlarged elevational view of a bone screw which constitutes a force transmitting member embodying one form of the invention and is driven into a tubular bone to urge a plate-like osteosynthetic accessory against the adjacent portion of the bone;

FIG. 2 illustrates a portion of the novel force transmitting member subsequent to breakage of its intermediate section;

FIG. 3 is an enlarged elevational view of a conventional bone screw which is driven into a bone corresponding to the bone of FIG. 1 and urges a plate-like osteosynthetic accessory against the adjacent portion of the bone;

FIG. 4 illustrates a portion of the bone screw of FIG. 3 subsequent to breakage of the bone screw adjacent the locus of penetration of its externally threaded shank into the bone;

FIG. 5 is an exploded elevational view of a two-piece force transmitting member embodying another form of the present invention and being designed to have its second section penetrate into a vertebra;

FIG. 6 illustrates a portion of a broken conventional force transmitting member which is designed to penetrate into a vertebra;

FIG. 7 is a fragmentary elevational view of a portion of a force transmitting member embodying a third form of the present invention;

FIG. 8 is a fragmentary partly perspective view of a force transmitting member embodying a further form of the present invention and cooperating with two clamping devices forming part of an osteosynthetic accessory; and FIG. 9 is a fragmentary perspective view of a force transmitting member which embodies an additional form of the invention and can be utilized, for example, in conjunction with the clamping devices of FIG. 8.

DESCRIPTION OF PREFERRED EMBODIMENTS

Referring first to FIG. 1, there is shown an osteosynthetic force transmitting member 1 which constitutes a bone screw and is constructed and configured in accordance with one embodiment of the present invention. The member 1 comprises a first section 2 which is in force-locking engagement with a bone B, a second section 3 which constitutes the head of the bone screw, and a third or intermediate section 4 between the sections 2 and 3. The first section 2 has an external thread 5 meshing with an internal thread in the adjacent portion of the bone B. The latter includes a relatively hard tubular portion 6 surrounding a medullary cavity 7. The second section or head 3 of the member 1 has a convex (substantially hemispherical surface 8 which bears against a complementary conical surface 9 in a recess 10 at the outer side of a plate-like osteosynthetic accessory 11 serving to urge the inner side of the accessory (hereinafter called plate for short) against the adjacent portion of the external surface 12 of the bone B.

The second section 3 (hereinafter called head for short) of the force transmitting member 1 has a centrally located recess or socket 13 bounded by a non-circular (e.g., hexagonal) surface engageable by the working end of a suitable tool which is used to, drive the first section 2 into or to withdraw the section 2 from the bone B. The socket 13 includes an extension or second socket 14 which is also bounded by a non-circular (e.g., pyramidal) surface and is provided in a first component 15 of the intermediate section 4. The latter further comprises a second component 16 which is of one piece with the component 15 as well as with the adjacent portion of the head 3. The intermediate section further comprises a weakened portion or breakage zone 17 where the member 1 should break in response to the application of excessive stresses to its sections, e.g., in response to the application of bending, tilting and/or shearing stresses to the head 3 by the plate 11. The component 15 is of one piece with the adjacent portion of the first section 2 and resembles a boss having a frustoconical external surface 18 which diverges in a direction from the section 2 toward the head 3, i.e., toward the component 16. The breakage zone 17 is located in the region where the socket 13 communicates with the extension or second socket 14.

As can be seen in FIG. 2, breakage of the member 1 in the region of the zone 17 exposes the surface 19 of the component 15 and thus affords access to the socket 14. Therefore, the socket 14 can receive a suitable tool which is used to extract the first section 2 of the member 1 from the bone B. The illustrated socket 14 can be replaced by a slot-shaped socket which can receive the working end of a standard screwdriver in order to rotate the component 15 in a direction to withdraw the first section 2 from the bone B.

The external surface 18 of the component 15 can be replaced with a polygonal (e.g. hexagonal) external surface which can be engaged by a wrench or another suitable tool for the purpose of extracting the section 2 from the bone B upon breakage of the member at the zone 17. Analogously, the head 3 can be provided with a polygonal or other non-circular surface which can be engaged by a wrench or another suitable tool in order to drive the first section 2 into or to withdraw the section 2 from the bone B prior to or in the absence of breakage of the member 1 at the zone 17. Such external profile can be provided on the head 3 in addition to or in lieu of the socket 13. Thus, the head 3 can be provided with a non-circular internal and/or external surface in order to move the first section 2 of an intact member 1 into or to extract the section 2 from a bone, such as the bone B, and the component 15 of the intermediate section 4 can also be provided with a non-circular external and/or internal surface in order to facilitate extraction of the section 2 from a bone subsequent to breakage of the member 1.

An important advantage of the improved force transmitting member 1 is that the breakage zone 17 is spaced apart from the adjacent portion of the external surface 12 of the bone B, even when the plate 11 is urged against such portion of the external surface 12, i.e., that the boss shaped first component 15 of the intermediate section 4 is fully accessible in the event of breakage of the member 1 along the selected zone 17. This renders it possible to extract the section 2 from the bone B without necessitating prior removal of bone material at that portion of the surface 12 which surrounds the component 15

Another advantage of the improved member 1 is that the socket 14 (if any) is also accessible in the event of breakage of the intermediate section 4 at the zone 17. The component 15 is then ready to be rotated by a tool which is introduced into the socket 14, by a tool (e.g., pliers) which engages the frustoconical external surface 18 of the component 15, or by a wrench which can engage the aforementioned non-circular external surface replacing the frustoconical external surface 18 of the component 15.

FIG. 3 illustrates a coventional force transmitting member 1a which lacks an equivalent of the intermediate section 4 of the improved member 1 of FIGS. 1 and 2. The head 3a of the member 1a is of one piece with the adjacent end portion of an elongated first section or shank 2a. The breakage zone 17a is disposed between the second and third turns of the thread 5a on the shank 2a. When the member 1a breaks (see FIG. 4), a portion of the thus exposed surface 19a is confined in the adjacent part of the hard tubular portions of the bone B. Therefore, if the section or shank 2a of the broken force transmitting member 1a is to be withdrawn from the bone B, it is necessary to machine a slot into the surface 19a and/or to remove bone material around such surface so that the external surface of the thus exposed portion of the shank 2a can be engaged by a torque transmitting tool which is to be used to rotate the shank 2a in a direction to extract it from the bone B.

The head 3a of the member 1a of FIGS. 3 and 4 has a relatively shallow recess 13a which does not sufficiently weaken the head to ensure that the application of excessive bending, shearing and/or other stresses to the member 1a would result in breakage of the head in the region surrounding the deepmost portion of the recess 13a instead of at the weakened or breakage zone 17a. The plate 11 of FIGS. 3 and 4 is or can be identical with the plate 11 of FIGS. 1 and 2. in FIG. 3, the passage 20 of the plate 11 spacedly surrounds that portion of the shank 2a which is of one piece with the head 3a. On the other hand, the passage 20 of the plate 11 shown in FIG. 1 receives the component 15 of the intermediate section 4 of the improved force transmitting member 1, preferably with a relatively small clearance. Since the junction of the component 15 with the adjacent end portion of the first section 2 can stand pronounced bending, shearing and/or other stresses, it is highly unlikely that the application of such stresses to the member 1 would result in a breakage between the component 15 and the section 2 rather than between the components 15, 16 of the intermediate section 4.

Removal of bone material around the breakage zone 17a is undesirable for several reasons. Thus such removal takes up a substantial amount of time and, even if the shank portion immediately adjacent the zone 17a becomes accessible it is still necessary to exert a large force in order to extract the shank 2a from the bone B because removal of bone material merely results in the exposure of one or more external threads 5a on the shank 2a. Furthermore, any removal of material from the bone B at the zone 17a of FIG.

4 entails a pronounced weakening of the bone B. This can necessitate transplantation of bone material in order to compensate for removal of material at the zone 17a of FIG. 4.

The improved force transmitting member 1 of FIGS. 1 and 2 is designed and produced in such a way that the breakage zone 17 is located at a certain distance away from the locus where the first section 2 penetrates into the bone B, namely at a distance which suffices to permit convenient engagement of the first component 15 of the intermediate section 4 by an available tool as soon as the member 1 breaks at the breakage zone 17. In other words, the weakest portion (zone 17) of the member 1 is positioned in such a way that it is spaced apart from the bone B even when the section 2 is driven into the bone to such an extent that the plate 11 bears against the adjacent portion of the external surface 12 of the bone and the head 3 bears against the concave surface at the outer side of the plate 11.

If the force transmitting member 1 is to constitute a surgical instrument, e.g., a bone drill, the head 3 constitutes a torque transmitting part of the instrument and the section 2 constitutes the actual drilling element. Again, the location of the breakage zone 17 is such that, if the instrument happens to break (e.g., in response to the application of excessive torque to the head 3), the zone 17 is still spaced apart from the locus of initial penetration of the tip of the section 2 into the bone so that the component 15 of the intermediate section 4 remains or becomes accessible for extraction of the section 2 from the bone if and when the need for extraction (without rotation of the section 2 by way of the head 3) arises. Such removal of the section subsequent to breakage of the instrument at the zone 17 does not necessitate any resection of the bone.

The breakage zone 17 can be obtained as a result of proper selection of the location and the depth of the recesses or sockets 13 and 14. In addition to or in lieu of such selection of the breakage zone 17, the latter can be established by removing material at the exterior of the intermediate section 4, e.g., by providing a groove in the external surface of the member 1 between the components 15 and 16 of the intermediate section 4.

The first component 15 of the intermediate section 4 may but need not constitute a boss whose diameter increases in a direction from one of the sections 2, 3 toward the other section, as long as it can stand stresses which cannot be withstood by the intermediate section 4 in the region of the desired or preselected breakage zone 17. The same holds true for the second component 16 of the intermediate section 4. Though the component 15 can be provided with an external threads, it is presently preferred to provide the component 15 with a smooth external surface 18 (as shown in FIGS. 1 and 2) or with the aforediscussed non-circular surface to facilitate engagement and rotation of the component 15 by resorting to an available tool (if and when the member 1 happens to break at the weakened or breakage zone 17).

FIG. 5 shows a novel and improved force transmitting member 101 which can be used with advantage to secure one or more osteosynthetic accessories to vertebrae. The first section 102 of the member 101 is provided with a customary thread 105 having a constant root diameter and a constant major diameter all the way to the component 115 of the intermediate section 104. The component 115 includes an externally threaded first part 115' which is of one piece with the section 102 and the root and major diameters of its thread vary (increase) in a direction from the section 102 toward the section 103. A second part 115" of the first component 115 has a polygonal external surface 118 which can be engaged by a tool when the section 102 is to be extracted from a vertebra subsequent to breakage of the member 101 at the preselected weakened or breakage zone 117 between the component 115 and the second component 116 of the section 104. The component 116 is of one piece with the component 115 as well as with the adjacent end portion of the second section 103.

The weakened or breakage zone 117 is obtained by providing the external surface of the intermediate section 104 with a circumferentially complete groove disposed between the polygonal part 115" of the component 115 and the component 116.

The external surface of a major part of the section 103 is provided with a standard machine thread 123 and its free end 121 constututes a polygonal element which can be engaged by a suitable tool to drive the section 102 into or to extract the section 102 from a vertebra. An osteosynthetic accessory (not shown in FIG. 5) can be located between a pressure transmitting surface or shoulder 125 of the part 115' of the component 115 and a nut 122 which can mesh with the externally threaded portion of the section 103. The external thread 123 of the section 103 and the internal thread 124 of the nut 122 are or can be selected in such a way that they establish a self-locking action and ensure that the nut 122 remains at a selected distance from the weakened or breakage zone 117 when the force transmitting member 101 is in actual use.

FIG. 6 shows a portion of a conventional force transmitting member 101a having a shank 102a which is to be driven into a vertebra. The breakage zone 117a is located between the end of the shank 102a and the adjacent hexagonal portion 121a of the second section 103a. The latter further comprises an elongated portion having a standard machine thread 123a adapted to mate with the internal thread of a nut, not shown in FIG. 6.

The member 101a exhibits the same drawbacks as the force transmitting member 1a of FIGS. 3 and 4. Thus, when the member 101a happens to break at the zone 117a, the shank 102a cannot be readily extracted because the zone 117a is at least partially received in the bone (not shown in FIG. 6). Therefore, it is necessary to machine a slot or another socket into the exposed surface of the shank 102a and/or to remove bone material around such surface.

The external thread 123 of the second section 103 of the improved force transmitting member 101 of FIG. 5 can be a standard ISO metric thread or a similar thread. The parameters (such as various diameters) of the thread 123 are selected in such a way that the member 101 is not likely to break across the section 103 but rather at the weakened zone 117, i.e., at a preselected locus of separation of the components 115, 116 from each other in response to the application of excessive forces to any one of the sections 102, 103, 104.

The weakened or breakage zones 17 and 117 can be established at the time the respective force transmitting member 1 or 101 is being mass produced in a plant or even at the locale of actual use. For example, the groove surrounding the weakened zone 117 of the force transmitting member 101 shown in FIG. 5 can be obtained by resorting to suitable clamping or like devices which have cutting or material displacing edges capable of adequately weakening the selected portion of the intermediate section of the improved force transmitting member. Such clamping or like devices can constitute osteosynthetic accessories, e.g., accessories which serve to couple the member 1 or 101 to a further accesory, such as a plate, a rod or any other part that is used to maintain the bone B or a vertebra in a desired position relative to the accessory or accessories and/or relative to one or more bones. It is also possible to employ two or more different force transmitting members as constituents of a complex implantation system. Thus, one of several force transmitting members can be designed to break at a selected location in response to the application of a relatively small force, and another of several force transmitting members can be designed to break at a selected locus in response to the application of a greater force.

FIG. 7 illustrates a portion of a third force transmitting member 201 which embodies the instant invention. The member 201 includes a second section 203 having at its free end (i.e., at the end remote from the intermediate section, not shown) a washer-like enlarged portion 226 provided with radially extending alternating ribs and grooves movable into mesh with the grooves and ribs of a complementary portion (not shown) provided on an osteosynthetic accessory of any suitable design. The two disc-shaped portions can be held together by a screw or bolt (not shown) extending through a tapped centrally located bore or hole 227 of the portion 226. The configuration of the first and intermediate sections of the force transmitting member 201 of FIG. 7 can be identical with or analogous to the configuration of the sections 2, 4 of the member 1 or of the sections 102, 104 of the member 101.

FIG. 8 illustrates a portion of a force transmitting member 301 which constitutes a modification of the member 101 of FIG. 5. All such parts of the member 301 which are identical with or clearly analogous to the corresponding parts of the member 101 are denoted by similar reference characters plus 200.

The section 303 of the member 301 of FIG. 8 has a standard metric thread 323 which extends between the hexagonal end portion 321 and the hexagonal part 315" of the component 315 forming part of the intermediate section 304. The weakened or breakage zone is or can be provider between the part 315" and the adjacent end portion (second component of the section 304) of the section 303. The section 303 is surrounded by two clamping devices 328, 329 respectively having jaws or claws 330, 331 which can engage and hold an osteosynthetic accessory such as a pin-shaped force transmitting member 401 shown in FIG. 9. The clamping device 328 is provided with a hexagonal passage 332 which can non-rotatably receive the hexagonal part 315" of the component 315 forming part of the intermediate section 304. The right-hand end of the section 303 can receive a nut (corresponding to the nut 122 shown in FIG. 5) in order to urge the clamping device 329 toward the clamping device 328 and to thus fix in a selected position an accessory which is located between and is engaged by the jaws or claws 330 and 331. The nut further serves to urge the clamping device 328 against the surface or shoulder 325 of the part 315' of the component 315.

The jaws or claws 330, 331 are provided with parallel internal ribs 333, 334, respectively, which can mate with complementary ribs 423 on the second section 403 of the pin-shaped force transmitting member 401 of FIG. 9. This ensures that the member 401 cannot rotate about its own longitudinal axis when the aforementioned nut urges the clamping device 329 toward the clamping device 328 so that the latter bears against the shoulder 325. The ribs 333, 334 can be replaced by or used jointly with otherwise configurated protuberances (e.g., with rasters) which cooperate with complementary protuberances (replacing or provided in addition to the ribs 423) to prevent rotation of the member 401 or an analogous pin or rod-shaped member relative to the jaws or claws 330, 331 when the aforementioned nut urges the clamping device 329 toward the clamping device 328 so that the latter is biased against the part 315' of the component 315. It is also possible to simply roughen the internal surfaces of the jaws or claws 330, 331 as long as they can non-rotatably engage an osteosynthetic accessory when the member 301 of FIG. 8 is in actual use.

At least one of the edge faces 335 on the jaw or claw 330 and/or at least one of the edge faces 336 on the jaw or claw 331 can be provided with a more or less pronounced cutting edge which penetrates into the material of an accessory (such as the member 401 of FIG. 9) when such accessory is located between and is engaged by the jaws of the clamping devices 328, 329. This prevents the member 401 or an analogous accessory from moving relative to the clamping devices 328, 329 in parallelism with the ribs 333, 334 as soon as the aforementioned nut is put to use to urge the devices 328, 329 toward the shoulder or surface 325.

The edge faces 335 and/or 336 can serve an additional useful purpose, namely to weaken one or more selected portions or zones of the clamped accessory (such as the member 401 of FIG. 9) in order to ensure that the member or accessory which is being clamped by the jaws 330, 331 will break at such selected location in response to the application of excessive stresses. In such instances, the provision of a pronounced weakened or breakage zone between the component 315 and the second component 316 of the section 304 is not absolutely necessary because the breakage, if any and if necessary, takes place at a distance from the bone (such as a vertebra) which receives the section 302 of the member 301.

The force transmitting member 401 of FIG. 9 resembles an elongated cylindrical pin and includes the aforementioned second section 403, a first section 402 and a smaller-diameter intermediate section 404. The diameter of the section 402 is or can be the same as the diameter of the section 403. The section 402 (and even the section 404) can be provided with external axially parallel ribs corresponding to the ribs 423 of the section 403.

The provision of the intermediate section 404 is optional if the aforediscussed edges 335 and/or 336 are designed to penetrate into and to thus weaken the corresponding portion or portions of the section 403 when the member 401 is clamped between the devices 328, 329 and serves as an accessory which connects the member 301 with one or more additional accessories of a system of accessories for properly locating one or more vertebrae receiving first section(s) of one or more force transmitting members 301.

It will be seen that a weakened or breakage zone can be provided during mass production of the improved force transmitting member (such as the member 1 or 101 or 401) or that such zone can be provided in a member (such as the member 401) when the latter is being put to actual use, e.g., when the member 401 (with or without the section 404) is clamped between the jaws 330, 331 of the devices 328, 329 with a force which suffices to provide one or more weakened zones in response to penetration of the edge faces 335 and/or 336 into the adjacent portion or portions of the member 401.

It is further possible to provide a plate-like osteosynthetic accessory with one or more preselected weakened or breakage zones. For example, the angle of divergence of the concave surface 9 in the upper side of the plate 11 shown in FIGS. 1 and 2 (relative to the surface bounding the passage 20) can be selected in such a way that the plate is likely to break where the passage 20 merges into the recess which is bounded by the concave surface 9. This reduces the likelihood of breakage of the member 1 at the zone 17 by the simple expedient of reducing the maximum resistance of the weakened zone of the plate 11 below the minimum resistance of the weakened or breakage zone 17. All that is necessary is properly select the angle of divergence of the concave surface 9 in a direction upwardly and away from the passage 20 (as seen in FIG. 1). The maximum resistance of the plate 11 to breakage is reduced by increasing the aforementioned angle. In fact, the weakened zone 17 can be dispensed with if the member 1 is used jointly with the plate 11 because the latter can be designed to break prior to transmission to the member 1 of forces or pressures such as would be likely to cause the member 1 to break at the section 2, 3 and/or 4 in such instance, the plate 11 constitutes a force transmitting member which embodies the present invention. By increasing the angle of divergence of the concave surface 9, the maker of the member 1 and plate 11 reduces the likelihood of secondary breakage of the member 1 (e.g., subsequent to a breakage of the plate 11) because the strongly divergent concave surface permits convenient and reliable separation of the broken plate 11 from the section 3 of the member 1.

Last but not least, it is possible to incorporate weakened or breakage zones into force transmitting members of the type disclosed in the commonly owned U.S. patent application Ser. No. 07/749,524 and in the corresponding European patent No. 0 472 017 B1 published Sep. 21, 1994.

The improved force transmitting member can be made of a single piece of a metallic or other suitable material or it can be made from a plurality of different materials. For example, and as shown in FIG. 1, the section 2 of the member 1 can include a metallic core 2a and an outer layer 2b made of another metallic material or of a non-metallic material, i.e., of a material other than the material of the core 2a. The core 2a and the outer layer 2b can extend all the way into the intermediate section 4 of the member 1. The layer 2b can consist of or can contain a fibrous material.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art and, therefore, such adaptations should and are intended to be comprehended within the meaning and range of equivalence of the appended claims.

What is claimed is:

1. An osteosynthetic force transmitting member comprising a first section arranged to force-lockingly engage a bone; a second section including means for coupling the force transmitting member to an osteosynthetic accessory; and an intermediate section disposed between said first and second sections and constituting a part of the force transmitting member weaker than adjacent portions of the first and second sections so that such intermediate section is more likely to break under overload conditions than said first and second sections in response to the application of forces to the force transmitting member, said intermediate section including first and second components which are of one piece with said first and second sections, respectively, and which establish between themselves a breakage zone said first component being accessible upon breakage of the force transmitting member at said breakage zone for direct engagement by a displacing tool serving to move said first section relative to the bone.

2. The force transmitting member of claim 1, wherein said first section includes means for anchoring the first section in a bone.

3. The force transmitting member of claim 2, wherein said anchoring means includes external projections provided on said first section.

4. The force transmitting member of claim 1, wherein said sections together constitute a cavity-forming surgical implement and said first section is arranged to penetrate into a bone.

5. The force transmitting member of claim 1, wherein said second section includes a profiled motion transmitting part which is engageable by a tool serving to effect a movement of said first section relative to a bone in the absence of breakage of said intermediate section.

6. The force transmitting member of claim 1, wherein said first component of said intermediate section has a surface configurated and positioned to receive and to transmit pressure to said first section.

7. The force transmitting member of claim 1, wherein said second section includes a first profiled motion transmitting part which is engageable by a tool serving to effect a movement of said first section relative to a bone in the absence of breakage of said intermediate section, said first component of said intermediate section including a second profiled motion transmitting part which is directly engageable by the displacing tool at least upon breakage of said intermediate section.

8. The force transmitting member of claim 7, wherein at least one of said profiled parts has a cross-sectional outline departing from a circular outline.

9. The force transmitting member of claim 7, wherein at least one of said profiled parts has an external profile departing from a circular profile.

10. The force transmitting member of claim 7, wherein at least one of said profiled parts has an internal profile departing from a circular profile.

11. The force transmitting member of claim 7, wherein at least one of said profiled parts includes a plurality of different portions engageable by tools serving to move the respective section relative to a bone which is form-lockingly engaged by said first section.

12. The force transmitting member of claim 7, wherein at least one of said profiled parts has a substantially conical surface.

13. The force transmitting member of claim 7, wherein at least one of said profiled parts has a substantially spherical surface.

14. The force transmitting member of claim 1, wherein at least a portion of said intermediate section has a cross section smaller than the cross sections of neighboring portions of said first and second sections.

15. The force transmitting member of claim 1, wherein at least one of said first and second sections comprises a plurality of discrete elements.

16. The force transmitting member of claim 1, wherein at least said first section has an external thread.

17. The force transmitting member of claim 1, wherein said first section includes a first portion having a first cross section and a second portion having a greater second cross section and being adjacent said first component of said intermediate section.

18. The force transmitting member of claim 17, wherein said second portion of said first section has a substantially conical, spherical or spheroidal outline.

19. The force transmitting member of claim 17, wherein said first section further includes a transition zone disposed between said first and second portions and having a smoothly curved outline.

20. The force transmitting member of claim 17, wherein said first section includes a thread having a root diameter and a major diameter, at least one of said diameters increasing toward sad intermediate section.

21. The force transmitting member of claim 1, wherein said first component of said intermediate section has a first cross section and said first section has a portion of one piece with and having a second cross section larger than the cross section of said first component.

22. The force transmitting member of claim 1, wherein said intermediate section has a polygonal outline.

23. The force transmitting member of claim 1, wherein said first section has a profiled surface adjacent said first component of said intermediate section.

24. The force transmitting member of claim 1, wherein said second section has an external thread.

25. An elongated osteosynthetic force transmitting member including a first end section engageable with a bone, a second end section engageable by a displacing tool to move said first end section relative to the bone, and an intermediate section having a first component of one piece with said first end section and a second component of one piece with said second end section and with said first component, said intermediate section further having a weakened portion disposed between said first and second components and being less resistant to breakage than the adjacent portions of said end sections and said first and second components, said first component of said intermediate section being configurated and dimensioned to be accessible to and to be engageable by an implement for the purpose of moving said first end section relative to a bone while said first end section engages such bone and subsequent to breakage of said weakened portion of said intermediate section.

* * * * *